US008834406B2

(12) United States Patent
Snyder et al.

(10) Patent No.: US 8,834,406 B2
(45) Date of Patent: Sep. 16, 2014

(54) BIOCOMPATIBLE GLAUCOMA DRAINAGE DEVICE

(71) Applicants: Robert W. Snyder, Tucson, AZ (US); John A. Martens, Tucson, AZ (US); Robert Munger, Arlington, TX (US)

(72) Inventors: Robert W. Snyder, Tucson, AZ (US); John A. Martens, Tucson, AZ (US); Robert Munger, Arlington, TX (US)

(73) Assignee: Snyder Biomedical Corporation, Tucson, AZ (US)

( * ) Notice: Subject to any disclaimer, the term of this patent is extended or adjusted under 35 U.S.C. 154(b) by 0 days.

(21) Appl. No.: 13/657,794

(22) Filed: Oct. 22, 2012

(65) Prior Publication Data

US 2014/0114226 A1   Apr. 24, 2014

Related U.S. Application Data

(60) Provisional application No. 61/627,954, filed on Oct. 21, 2011.

(51) Int. Cl.
| | | |
|---|---|---|
| *A61F 9/00* | (2006.01) | |
| *A61F 9/007* | (2006.01) | |
| *A61F 2/14* | (2006.01) | |
| *A61M 27/00* | (2006.01) | |
| *A61F 9/008* | (2006.01) | |

(52) U.S. Cl.
CPC .............. *A61F 9/00781* (2013.01); *A61F 9/007* (2013.01); *A61F 9/0017* (2013.01); *A61F 2/14* (2013.01); *A61M 27/002* (2013.01); *A61F 2009/00891* (2013.01); *A61F 2210/0057* (2013.01); *A61F 2210/0076* (2013.01); *A61F 2220/0008* (2013.01); *A61F 2220/0016* (2013.01); *Y10S 623/905* (2013.01)
USPC .................... 604/8; 604/9; 604/294; 623/4.1; 623/5.11; 623/905

(58) Field of Classification Search
CPC ................ A61F 9/00781; A61F 9/007; A61F 2009/00891; A61F 2210/0061; A61F 2210/0076; A61F 2220/0016; A61F 9/0017; A61F 9/0008; A61F 2/14; A61F 2002/14; Y10S 623/905
USPC ............. 604/8, 9, 10, 294; 623/1.1, 4.1, 5.11, 623/23.64
See application file for complete search history.

(56) References Cited

U.S. PATENT DOCUMENTS

| | | | | |
|---|---|---|---|---|
| 5,171,213 | A | 12/1992 | Price | |
| 5,893,837 | A * | 4/1999 | Eagles et al. | 604/9 |
| 2002/0156413 | A1* | 10/2002 | Williams et al. | 604/8 |
| 2003/0236483 | A1 | 12/2003 | Ren | |
| 2004/0181240 | A1* | 9/2004 | Tseng et al. | 606/119 |
| 2006/0036207 | A1* | 2/2006 | Koonmen et al. | 604/8 |
| 2006/0079828 | A1 | 4/2006 | Brown | |
| 2006/0276739 | A1* | 12/2006 | Brown | 604/8 |
| 2007/0078371 | A1 | 4/2007 | Brown et al. | |
| 2007/0088432 | A1* | 4/2007 | Solovay et al. | 623/4.1 |

(Continued)

OTHER PUBLICATIONS

PCT/US2012/061390—International Search Report and Written Opinion dated Feb. 25, 2013.

*Primary Examiner* — Adam Marcetich
(74) *Attorney, Agent, or Firm* — Dale F. Regelman; Quarles & Brady LLP (57) ABSTRACT

A biocompatible glaucoma drainage device, comprising a non-porous element, a porous element, an anchoring assembly disposed around the non-porous element, wherein the anchoring assembly comprises a plurality of barbs extending outwardly therefrom.

7 Claims, 7 Drawing Sheets

(56) References Cited

U.S. PATENT DOCUMENTS

| | | |
|---|---|---|
| 2007/0293872 A1 | 12/2007 | Peyman |
| 2008/0161741 A1* | 7/2008 | Bene et al. ............ 604/9 |
| 2008/0228127 A1* | 9/2008 | Burns et al. ............ 604/9 |
| 2009/0326470 A1 | 12/2009 | Rosenberg et al. |
| 2010/0004635 A1 | 1/2010 | Lin et al. |
| 2010/0087774 A1* | 4/2010 | Haffner et al. ............ 604/8 |
| 2010/0209477 A1* | 8/2010 | Butuner et al. ............ 424/427 |
| 2012/0035525 A1* | 2/2012 | Silvestrini ............ 604/8 |
| 2012/0245505 A1* | 9/2012 | Robinson et al. ............ 604/8 |
| 2013/0267887 A1* | 10/2013 | Kahook et al. ............ 604/9 |
| 2013/0324942 A1* | 12/2013 | de Juan et al. ............ 604/246 |

* cited by examiner

BIOCOMPATIBLE GLAUCOMA DRAINAGE DEVICE

CROSS-REFERENCE TO RELATED APPLICATIONS

This Non-Provisional application claims priority to a U.S. Provisional Application filed Oct. 21, 2011 and having Ser. No. 61/627,954.

FIELD OF THE INVENTION

The present invention is directed to implants, and in particular to a glaucoma drainage device. In addition, the invention is further directed to a method to form Applicants' glaucoma drainage device. Furthermore, the invention is directed to a method to implant into a subject in need thereof Applicants' glaucoma drainage device

BACKGROUND OF THE INVENTION

Glaucoma is a disease where the nerve fibers that form the optic nerve degenerate over time and cause loss of sight corresponding to the areas of the retina from which the nerve fibers transmit the photopic stimulation. Elevated intraocular pressure (IOP) is the primary risk factor for degeneration of these nerve fibers and reduction of the interocular pressure is the primary goal of treatment to prevent further loss of optic nerve tissue and the associated visual loss.

Vision loss from glaucoma can be delayed or prevented in most patients by lowering the intraocular pressure. This may be accomplished by using topical medications, laser treatment or trabeculectomy to increase an outflow of aqueous humor from the anterior chamber of the eye. When these methods fail to control intraocular pressure, ophthalmic surgeons may use aqueous drainage devices or "glaucoma shunts" to facilitate movement of aqueous humor from the anterior chamber to outside the eye and thus reduce high levels of intraocular pressure. Currently, these devices are used as a secondary intervention because some believe they have a relatively high complication and failure rate.

SUMMARY OF THE INVENTION

A glaucoma drainage device is presented, wherein that device is biocompatible and physically shaped such that it can be placed with minimal tissue disruption and is self-secured in an appropriate position. The surgical procedure benefits of this design include: (1) a small tangential conjunctival and scleral incisions are made rather than requiring a circumferential incision, and (2) there is minimal disruption of the blood or lymph channels which carry fluid away from a reservoir or distal end.

Applicants' glaucoma drainage device comprises an inner porous element, an overlapping outer porous element (overlapping the inner porous element), bonded to a non-porous tubular member. The non-porous tubular member functions as a catheter facilitating the outflow of aqueous humor from the anterior chamber of the eye to a region external to the anterior chamber. In certain embodiments, the first and second porous elements may include, for example, expanded polytetrafluoroethylene (ePTFE), polyurethane, and elastomeric silicone.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF PREFERRED EMBODIMENTS

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Described methods generally set forth as logical flow steps. As such, the depicted order and labeled steps are indicative of one embodiment of the presented method. Other steps and methods may be conceived that are equivalent in function, logic, or effect to one or more steps, or portions thereof, of the illustrated method. Additionally, any format and symbols employed are provided to explain the logical steps of the method and are understood not to limit the scope of the method. Although various arrow types and line types may be employed in any flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Conventional glaucoma shunts, such as those disclosed in U.S. Pat. Nos. 5,338,291 and 5,476,445, both of which are incorporated herein by reference, include a catheter (i.e., a drainage tube) attached to a base plate. A free end of the catheter is surgically implanted into the anterior chamber of the eye. The base plate is sutured to an outer surface of the globe beneath the conjunctiva. The glaucoma implant functions as a drain over the first three to six postoperative weeks and ultimately the silicone or PMMA stimplate is enclosed by a fibrous capsule.

Ideally, the capacity for fluid outflow of the fibrous capsule (i.e., the filtering bleb) that surrounds the base plate is such that the amount of fluid that passes through the capsule is sufficient to reduce the intraocular pressure to a safe level. In this case, aqueous humor can be drained from the anterior region of the eye, through the drainage tube to the reservoir device, escape into the surrounding tissue where it is absorbed.

Conventional glaucoma shunts are formed of silicone or polypropylene, materials approved for human implant use, but which stimulate fibroblast activation and scar formation when the material is implanted on the sclera underneath the conjunctiva of the eye. The scarring around the distal portion of the device produces a fibrous capsule that may "wall off" the device from the normal vessels and prevent the flow of fluid and the function of the device may decline over time. In this case the primary cause of failure is a foreign body tissue response to the silicone or polypropylene material which results in encapsulation of the drainage reservoir.

Applicants' glaucoma drainage device comprises porous elements on a distal end, so that new blood vessel growth occurs in pores, channels, or interstices of the porous material (after denucleation to remove entrapped air). These new vessels do not have tight junctions and thus will carry away fluid and aid in fluid outflow. In addition, Applicants' glaucoma drainage device has a long-term life expectancy.

In addition, Applicants' glaucoma drainage device comprises a biocompatible, flexible, self-anchoring assembly on a proximal end that eliminates movement of the device into or out of the eye after placement.

Applicants' glaucoma drainage device comprises an inner porous element, an overlapping outer porous element (overlapping the inner porous element), bonded to a non-porous tubular member. The non-porous tubular member functions as a catheter facilitating the outflow of aqueous humor from the anterior chamber of the eye to a region external to the anterior chamber. In certain embodiments, the outer porous element comprises, for example, expanded polytetrafluoroethylene (ePTFE), polyurethane, and elastomeric silicone, which have pores with diameters within a range of about 1 micron to about 500 microns, and preferably from 30 microns to about 60 microns In certain embodiments, the inner porous element comprises expanded polytetrafluoroethylene (ePTFE), polyurethane, and/or elastomeric silicone, which have pores with diameters greater than or equal to about 30 microns and preferably in the range of 40 to 60 microns. In certain embodiments, the connected inner and outer porous elements regions comprise a permeability defined as a water flow through rate of at least 1.0 microliter/min·cm² at a water entry pressure of 100 mm Hg. (The human aqueous fluid is produced at a rate of approximately 1 microliter/minute and the dimensions and out flow must provide for this aqueous production).

In certain embodiments, Applicants' glaucoma drainage device further comprises a flexible, self-anchoring assembly, like a double catch on a cactus barb to prevent extrusion of the glaucoma drainage device after placement.

Also provided is a method of making Applicants' glaucoma drainage device. The method includes bonding of non-porous tubing to porous tubing using a flared joint wherein the non-porous tubing is flared, the porous tubing is mechanically stretched over the flare, following by a heat bonding or thermal annealing step to anchor the non-porous tubing in place or otherwise remove thermal stresses that may otherwise lead to a loose connection between the two tubing types. A thermal bonding ring may also be incorporated to ensure the anchorage using a thermoplastic material with a lower softening temperature (Vicat softening temperature) than either the porous or non-porous materials. The thermal bonding ring can act as a heat shrinkable material so that after placement and when heated to its' heat relaxation temperature, shrinkage occurs that further ensures mechanical fixturing of the porous material(s) to the underlying non-porous materials. In addition, a method of treating glaucoma using the above-noted novel glaucoma drainage device is provided. This method includes surgically inserting one end of the catheter into the anterior chamber of the eye, beneath the conjunctiva providing connection to the region where aqueous humor is produced. The outflow path of aqueous humor from this region will then be modified to include a pathway through the device to the porous region on its distal end and then to the tissues that normally convey outflow.

Figure 1:
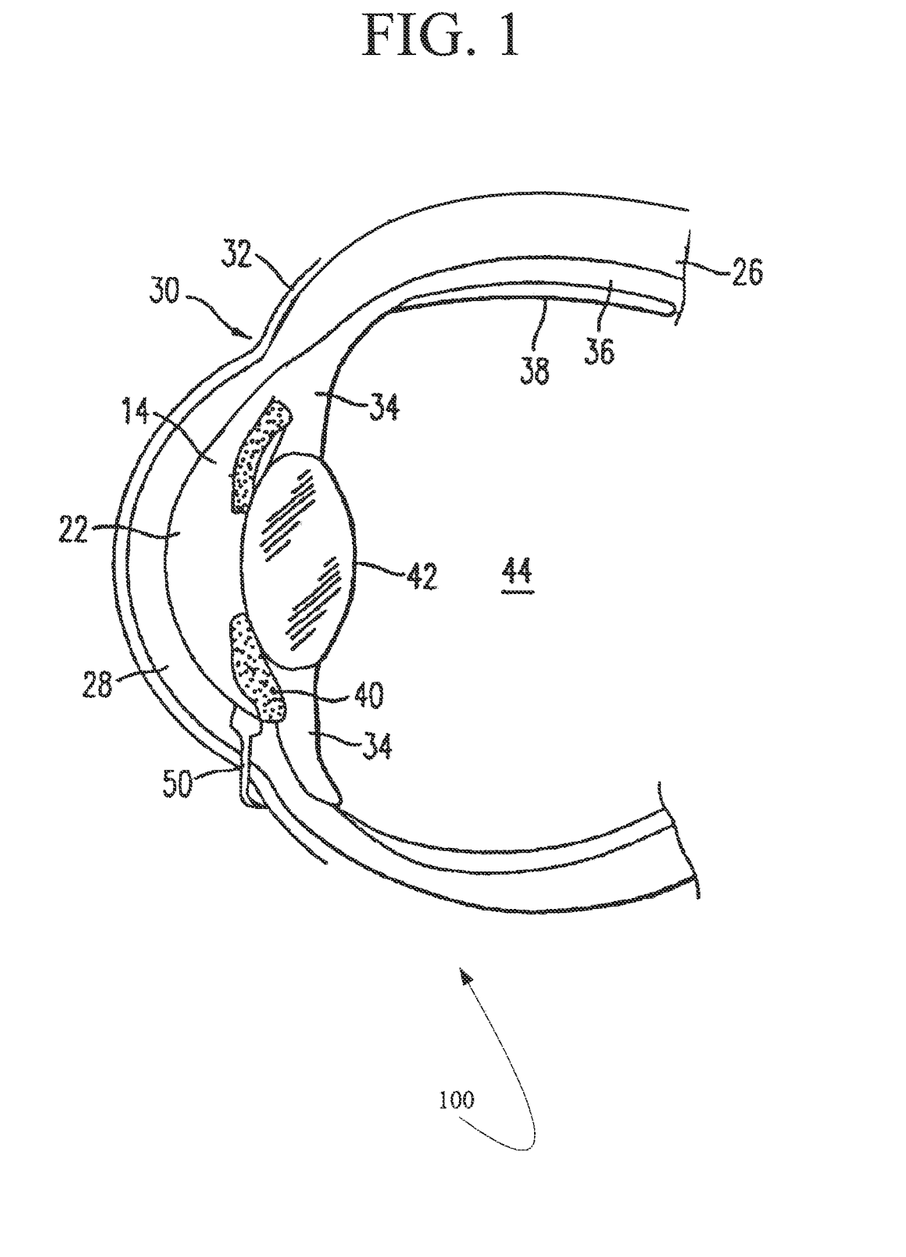
FIG. 1 illustrates the anatomy of the human eye.

Referring now to FIG. 1, human eye 100 includes an anterior chamber 22 located between a cornea 28 and a lens 42. The cornea 28 merges into a sclera 26 at limbus 30. Conjunctiva 32 extends from the limbus 30 over the front half of the eye to a position underlying the upper and lower eyelids.

Ciliary body 34 extends rearwardly until it becomes a choroid 36. The Choroid region 36 comprises many blood vessels. Iris 40 controls an amount of light reaching lens 42 which is disposed behind iris 40. A central portion of the eye 100 rearward of the lens 42 is called a vitreous cavity 44, whereas the portion forward of the iris 40 is called the anterior chamber 22. The anterior chamber 22 includes aqueous humor, which is a thin, watery eye fluid.

Aqueous humor is generated primarily by the ciliary body 34. In a normally functioning eye, this fluid is continuously drained to maintain a sufficient constant intra ocular pressure. The fluid drains through a trabecular meshwork (not shown), into the Schlemm canal 50, and out into the veins and lymphatic channels leaving the eye 100. Glaucoma results when this fluid does not properly drain.

Figure 2:
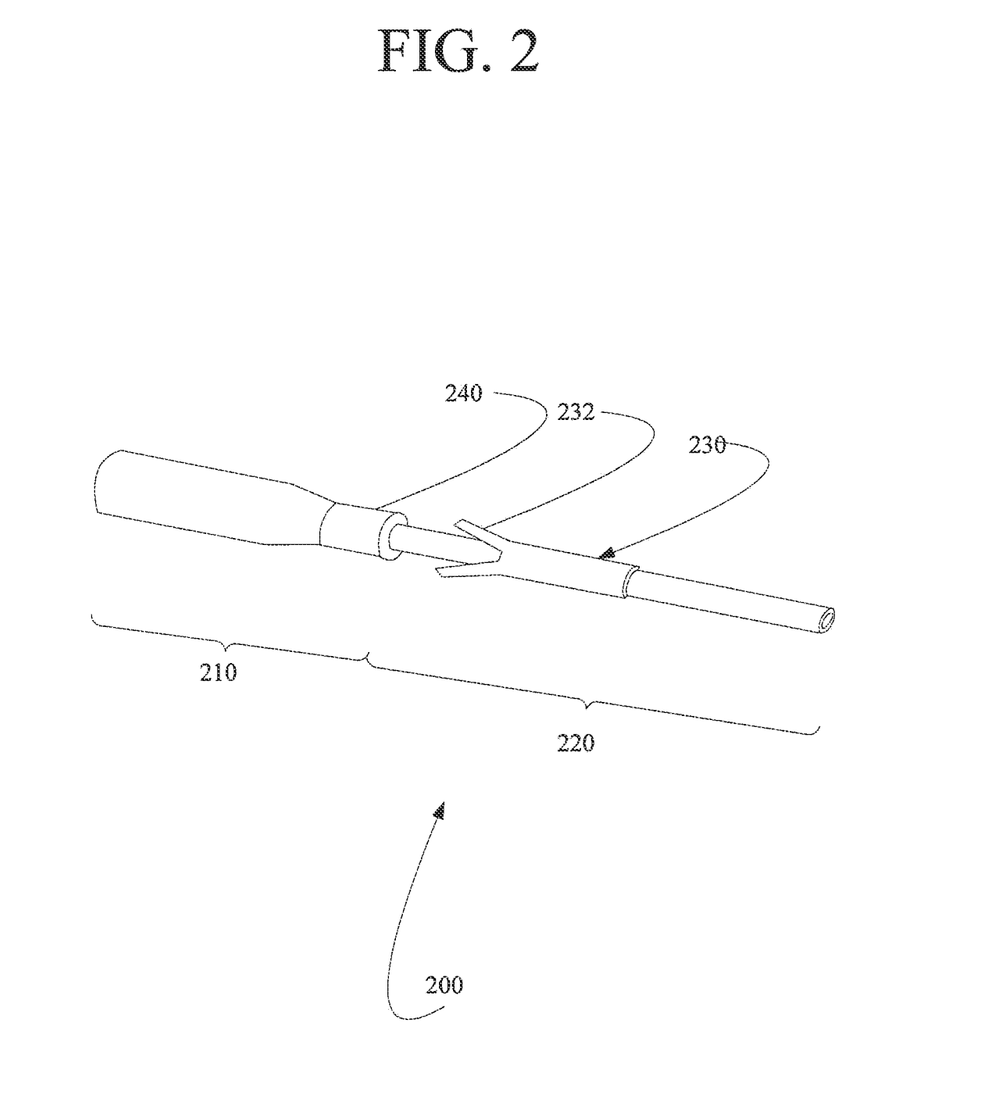
FIG. 2 illustrates Applicants' glaucoma drainage device.

Referring now to FIG. 2, Applicants' glaucoma drainage device 200 includes a porous assembly 210, a porous or non-porous assembly 220, and an anchoring assembly 230 comprising a plurality of raised barbs 232. Anchoring assembly 230 is disposed around the porous or non-porous assembly 220. In certain embodiments, the porous or non-porous assembly 220 and anchoring assembly 230 are integrally molded and comprise a single structure.

The anchoring assembly 230 may be provided by a separate tubular element containing the barbs 232 that is slid over the catheter element 330 (FIG. 3) and thermally bonded to it, or by virtue of using a larger outer diameter catheter tube with the barb elements fashioned into it via manipulation of the exterior region of the tube.

Other utilities of the anchoring assembly 230 include stabilization of any indwelling tissue catheter or device such as but not limited to intravenous, intraarterial, intrathecal, intratympanic membrane, or intraabdominal, shunts into or out of the abdomen, the skull, the dura or ventricals of the brain, the bladder, the posterior eye, the sinuses, the chest cavity, the scrotum, the ureter, peritoneum, the nose or nasal passages, the trachea for intubation or external tracheostomy or the inner ear. Additionally anchoring assembly 230 could be used to aid in stripping varicose veins, cleaning intra arterial plaque or intra vascular clots. Anchoring assembly 230 can be used as an aid in providing intermediate or long term drains and fistulas from any body cavities or spaces, including drainage of closed compartments as seen in the leg following crush injuries, trauma, thermal or chemical injury or chronic abscess or focal inflammations.

In addition anchoring assembly 230 can be coupled as a pair and disposed on a distal end to distal end to prevent migration of a stent placed anywhere in the body or a connected tube.

Anchoring assembly 230 220 can also be added to a reservoir such as seen with the ahmed, molteno, baerveldt, or glaucous glaucoma devices.

Figure 3:
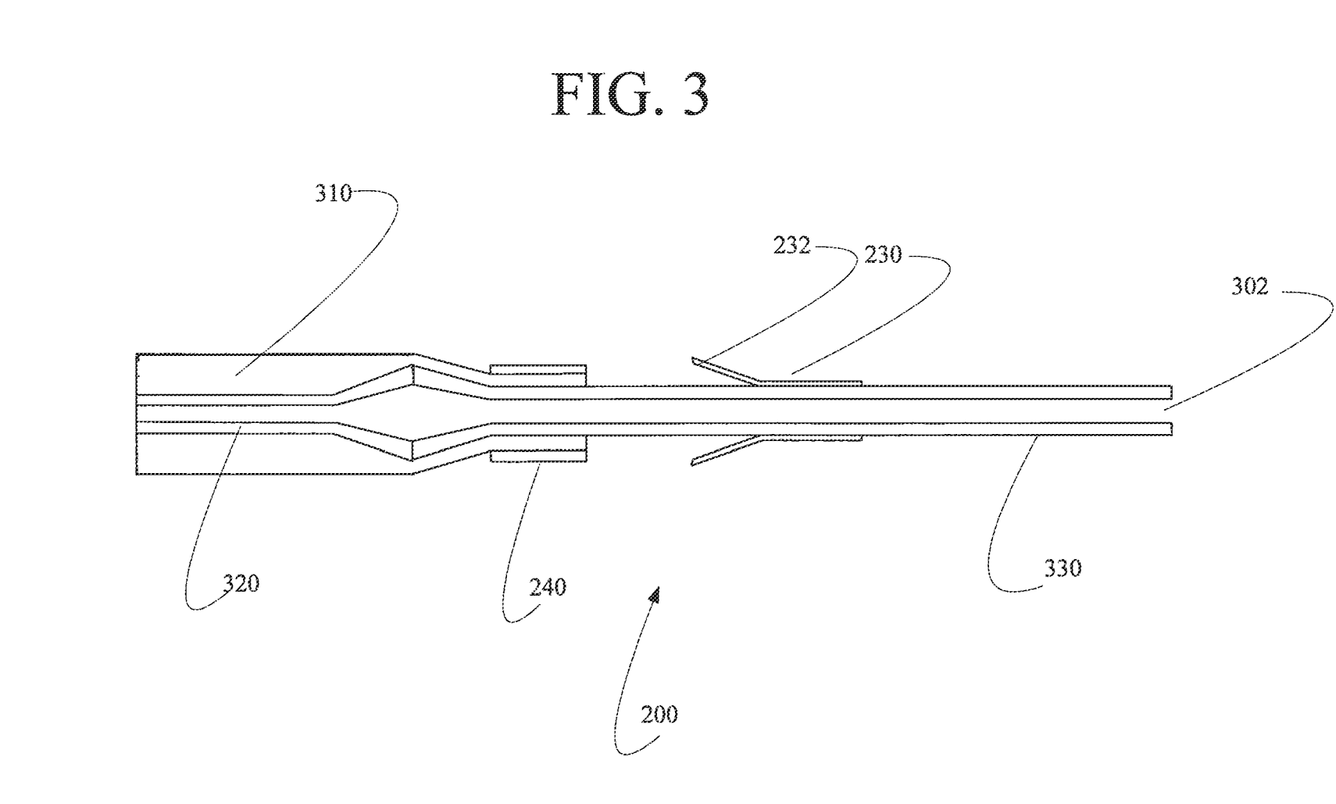
FIG. 3 is a cross-sectional view of the glaucoma drainage device of FIG. 2.

Referring now to FIG. 3, porous assembly 210 comprises a first porous element 310 and a second porous element 320. Non-porous assembly 220 comprises catheter 330.

Bonding element 240 is disposed around a distal end of first porous element 310 which encircles a portion of catheter 330. Bonding element 240 provide anchorage of first porous element 310 to catheter 330. In certain embodiments, bonding element 240 is thermally bonded to first porous element 310. In certain embodiments, bonding element 240 is thermally bonded to both first porous element 310 and catheter 330.

Porous assembly 210 comprises a plurality of porous elements. In the illustrated embodiment of FIG. 3, porous assembly 210 comprises first porous element 310 which overlies second porous element 320. In certain embodiments, the plurality of porous elements comprising porous assembly 210 are attached to one another by, for example and without limitation, laminating or bonding the elements together.

The architecture of FIG. 3 should not be taken as limiting. In certain embodiments, porous assembly 210 comprises more than 2 porous elements. For example and without limitation, in certain embodiments porous assembly 210 comprises a first, second and third porous elements. In certain embodiments, those first, second, and third porous elements comprises individual layers (i.e., first, second and third layers). In certain embodiments, those first, second, and third porous elements comprise a single structure comprising a plurality of regions or zones of differing porosity.

Figure 5:
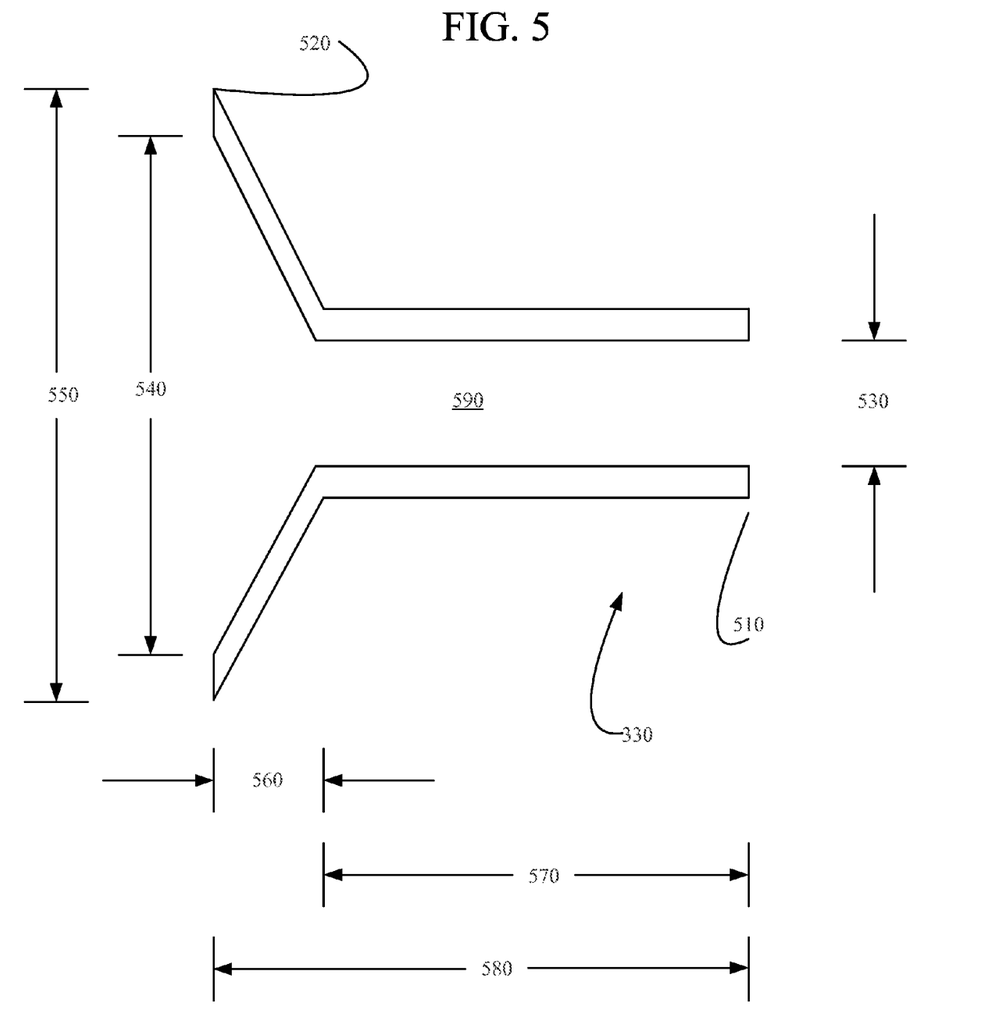
FIG. 5 illustrates a non-porous tubular member disposed in the glaucoma drainage device of FIGS. 2 and 3.

Referring now to FIG. 5, catheter 330 comprises open first end 510, an opposing open second end 520, and lumen 590 interconnecting first end 510 and second end 520. Catheter 330 is formed at first open end 510 to include aperture 302. Lumen 550 comprises an internal diameter 530 at aperture 302. In certain embodiments, internal diameter 530 is between about 0.3 mm and about 0.5 mm. In certain embodiments, internal diameter 530 is about 0.4 mm.

Catheter 330 comprises a length 580. In certain embodiments, length 580 is between about 2.0 mm and about 8.0 mm. In certain embodiments, length 580 is about 5.0 mm.

In the illustrated embodiment of FIGS. 3 and 5, catheter 330 is formed to include a tubular member 502, conical portion 504, and second end 520. Conical portion 504 comprises a length 560. In certain embodiments, length 560 is between about 1.0 mm and about 3.0 mm. In certain embodiments, length 560 is about 5.0 mm.

Tubular member 502 comprises a length 570. In certain embodiments, length 570 is between about 2.0 mm and about 6.0 mm. In certain embodiments, length 570 is about 5.0 mm.

The illustrated lengths 560, 570, and 580, and the illustrated widths 530, 540, and 550, in FIG. 5 are not representative of actual lengths and widths of Applicants' glaucoma drainage device. Rather, illustrated lengths 560, 570, and 580, and the illustrated widths 530, 540, and 550, are used only for demonstrative purposes. These illustrated lengths and widths should not be taken as limiting.

Second end 520 comprises an outer diameter 550 and an internal diameter 540. In certain embodiments, outer diameter 550 is between about 0.8 mm and about 1.4 mm. In certain embodiments, outer diameter 550 is about 1.0 mm. In certain embodiments, internal diameter 540 is between about 0.6 mm and about 1.2 mm. In certain embodiments, internal diameter 540 is about 0.9 mm.

Figure 6:
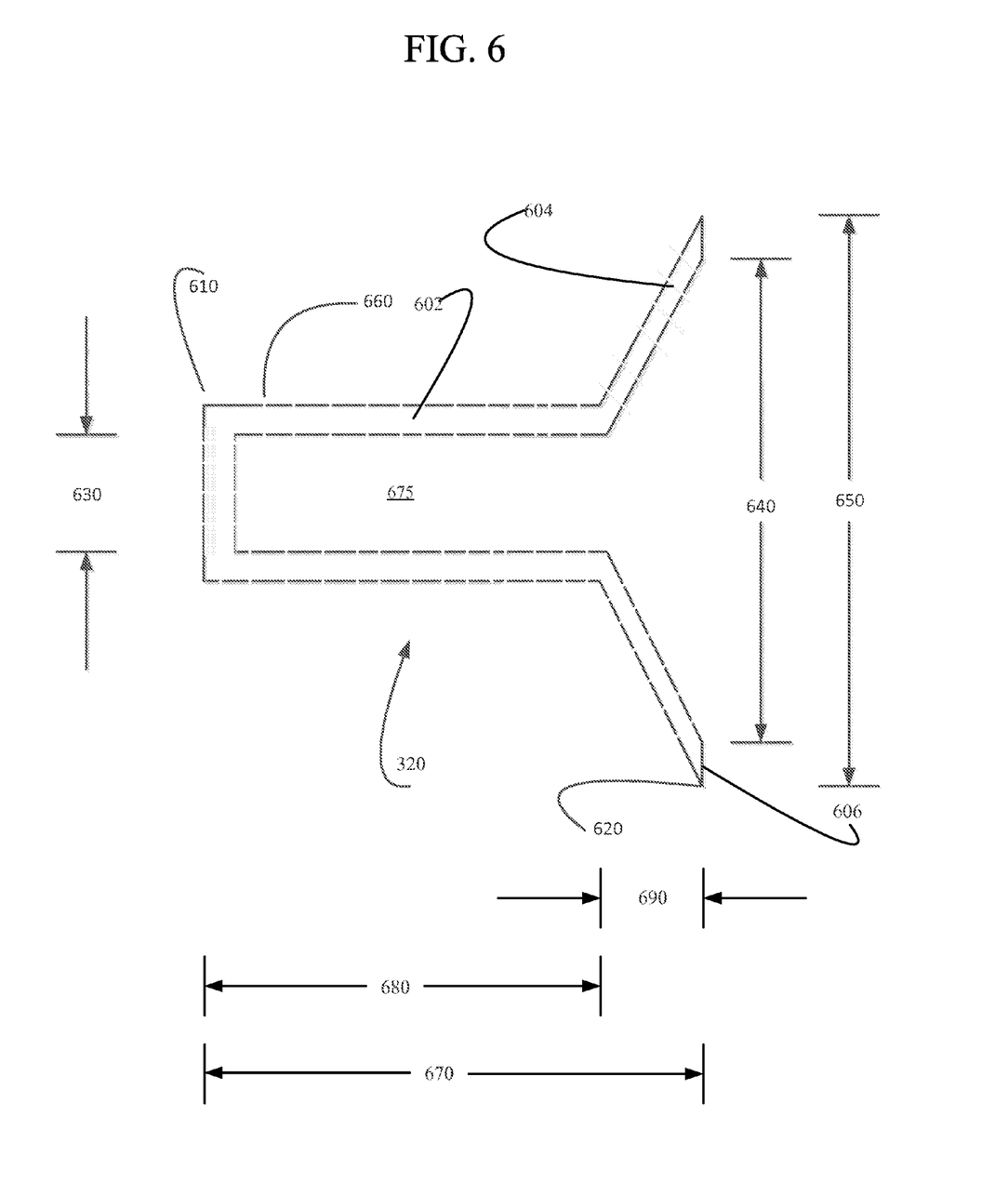
FIG. 6 illustrates the a first porous tubular member disposed in the glaucoma drainage device of FIGS. 2 and 3.

Referring now to FIG. 6, second porous element 320 comprises a tubular member 602, a conical portion 604, open first end 620, opposing closed or open second end 610, and internal bore 675. Bore 675 comprises a diameter 630 at closed end 610. In certain embodiments, diameter 630 is between about. 0.4 mm and about 0.8 mm. In certain embodiments, diameter 630 is about 0.6 mm.

Second porous element 320 comprises a length 670. In certain embodiments, length 670 is between about 2.0 mm and about 8.0 mm. In certain embodiments, length 670 is about 0.5 mm.

Conical portion 604 comprises a length 690. In certain embodiments, length 690 is between about 0.5 mm and about 2.0 mm. In certain embodiments, length 690 is about 1.0 mm.

Tubular member 602 comprises a length 680. In certain embodiments, length 680 is between about 1.0 mm and about 6.0 mm. In certain embodiments, length 680 is about 2.0 mm.

Second end 620 comprises an outer diameter 650 and an internal diameter 640. In certain embodiments, outer diameter 650 is between about 0.8 mm and about 1.4 mm. In certain embodiments, outer diameter 650 is about 1.0 mm. In certain embodiments, internal diameter 640 is between about 0.6 mm and about 1.2 mm. In certain embodiments, internal diameter 640 is about 0.9 mm.

The illustrated lengths 670, 680, and 690, and the illustrated widths 630, 640, and 650, in FIG. 6 are not representative of actual lengths and widths of Applicants' glaucoma drainage device. Rather, illustrated lengths 670, 680, and 690, and the illustrated widths 630, 640, and 650, are used only for demonstrative purposes. These illustrated lengths and widths should not be taken as limiting.

Second porous element 320 comprises a plurality of pores 660 extending therethrough. The pores 660 shown in FIG. 6 are depicted as straight, regular channels. The illustrated embodiment of FIG. 6 should not be taken as limiting. Rather, the plurality of pores 660 depicted is meant to illustrates the porosity of second porous element 320. Those skilled in the art will appreciate that each of the plurality of pores 660 comprises an irregular shape, and is irregularly spaced along and through tubular member 602, conical portion 604, and closed end 610.

In certain embodiments, but not all designs of the device, each of the plurality of pores 660 comprises a diameter less that or equal to about 0.8 microns. Each of pores 660 is formed to comprise a diameter too small to permit cellular entry therethrough. In certain embodiments, the plurality of pores 660 is formed using leachable salt inclusion at the time of polymer extrusion. In certain embodiments, the plurality of pores 660 is formed by physically creating pores or channels using mechanical devices, such as drills, or by optical devices, such as lasers.

Referring now to FIGS. 3, 5, and 6, in certain embodiments flared end 520 of catheter 330 is attached to flared end 620 of second porous element 320. In certain embodiments, edge 506 is attached to edge 606 using an adhesive. In certain embodiments, edge 506 is thermally fused to edge 606.

In certain embodiments, edge 506 is stretched to extend over edge 606. In these embodiments, the porous tubing is mechanically stretched over the flare, followed by a heat bonding or thermal annealing to anchor the non-porous tubing in place or otherwise remove thermal stresses that may otherwise lead to a loose connection between the two tubing types. In certain embodiments, a thermal bonding ring is also utilized to ensure the anchorage using a thermoplastic material with a lower softening temperature (Vicat softening temperature) than either the porous or non-porous materials. The thermal bonding ring can act as a heat shrinkable material so that after placement and when heated to its' heat relaxation temperature, shrinkage occurs that further ensures mechanical fixturing of the porous material(s) to the underlying non-porous materials.

Figure 7:
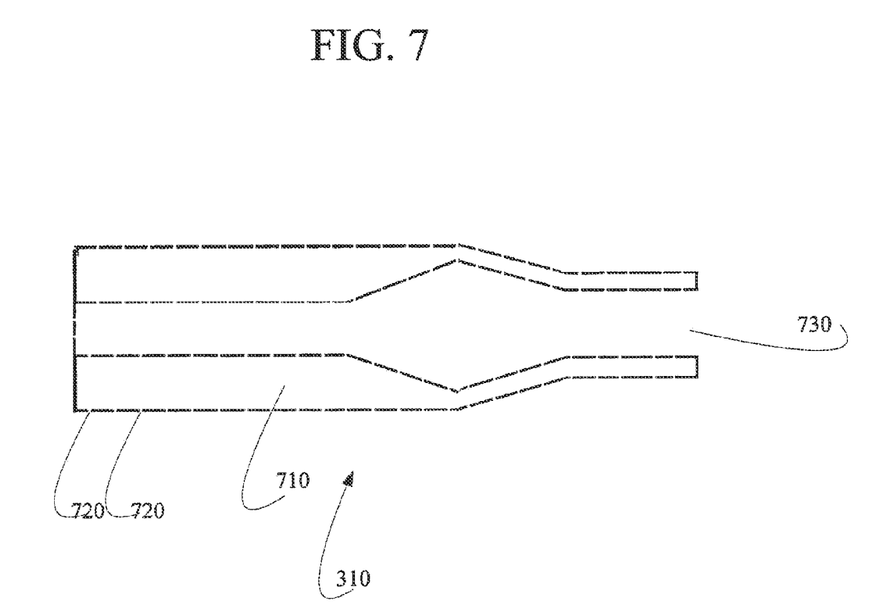
FIG. 7 illustrates a second porous tubular member disposed in the glaucoma drainage device of FIGS. 2 and 3.

Referring now to FIG. 7, first porous element 310 comprises a plurality of pores 720 extending through. The pores 720 shown in FIG. 7 are depicted as straight, regular channels. The illustrated embodiment of FIG. 7 should not be taken as limiting. Rather, the plurality of pores 720 depicted is meant to illustrate the porosity of first porous element 310. Those skilled in the art will appreciate that each of the plurality of pores 720 comprises an irregular shape, and is irregularly spaced along and through a material 710.

In certain embodiments, material 710 comprises a polymeric material such as ePTFE of pore size 10-100 microns (ideal being 30-60 microns).

Each of the plurality of pores 720 comprises a diameter sufficient to allow blood vessels to pass through. In certain embodiments, each of the plurality of pores 720 comprises a diameter within a range of about 1 micron to about 500 microns. In certain embodiments, the plurality of pores 720 is formed using leachable salt inclusion at the time of polymer extrusion. In certain embodiments, the plurality of pores 720 is formed by physically creating pores or channels using mechanical devices, such as drills, or by optical devices, such as lasers.

In certain embodiments, the material used to form the first porous element is selected from the group consisting of expanded polytetrafluoroethylene (ePTFE), polyurethane, and elastomeric silicone.

In addition, the pores or channels of ePTFE may also be referred to as "intermodal distances," which is considered a measure of porosity. A more detailed description of intermodal distances is described in the document "The Effects of Porosity on Endothelialization of ePTFE Implanted in Subcutaneous and Adipose Tissue" by Salzman et al, J. Biomed. Mater. Res., which is herein incorporated by reference in its entirety.

In addition, the connected first and second porous elements 310 and 320 include a permeability defined as a water flow through rate of at least 1.0 microliter/min·cm$^2$ at a water entry pressure of 100 mmHg, to allow a minimum of 1 microliter per minute at 10 mm hg to flow through the entire system, which provides an assessment of relative porosity. In certain embodiments, catheter 330 is formed from silicone, ePTFE, polycarbonate, polyethylene, polyurethane, or any combination thereof, and have an inner diameter sufficient to allow flow of aqueous humor from the anterior chamber 22 to the hollow reservoir, such as a diameter of about 0.04 to 0.4 mm, for example.

Figure 4:
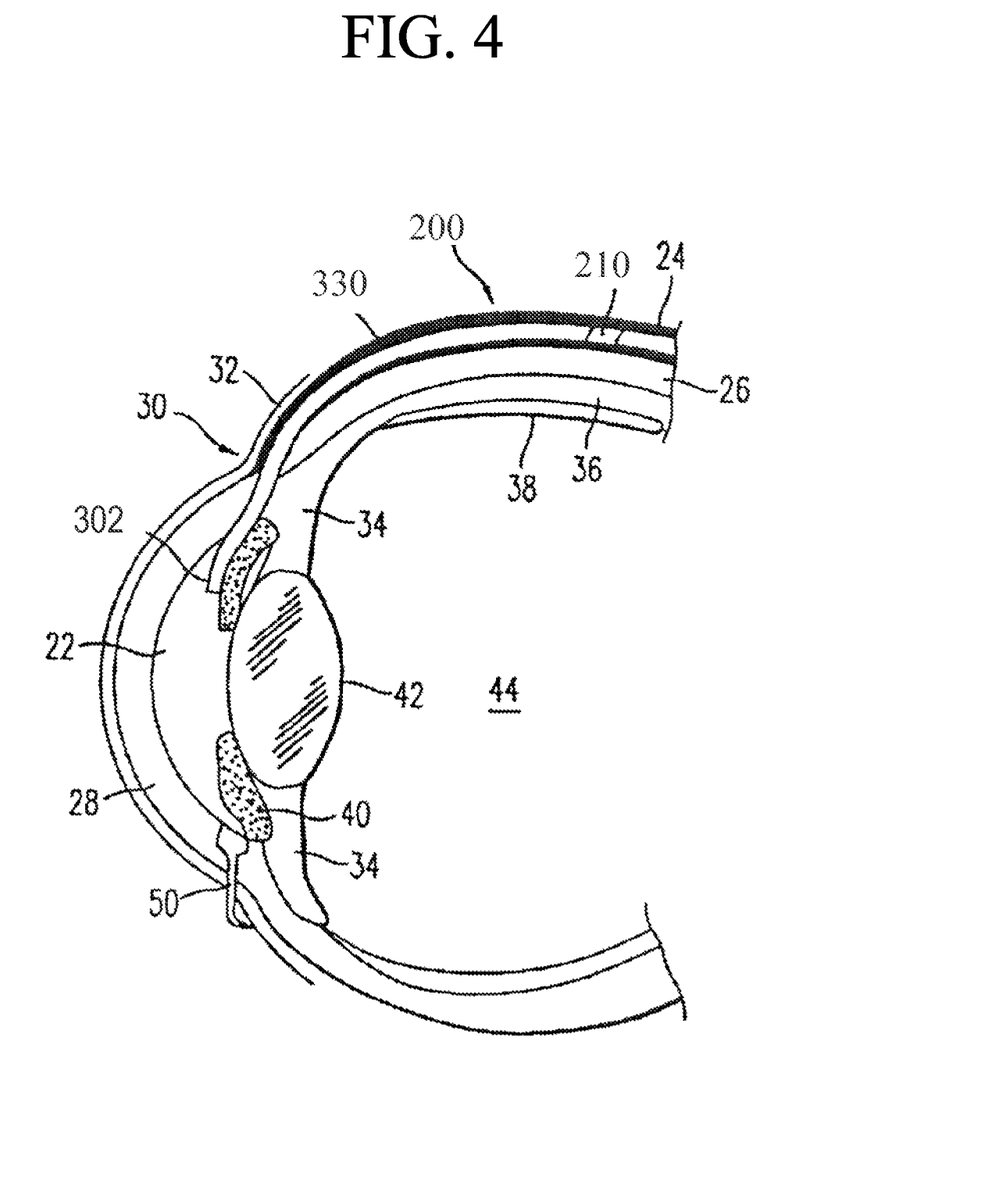
FIG. 4 illustrates the glaucoma drainage device of FIGS. 2 and 3 surgically implanted into the eye of FIG. 1.

Referring now to FIG. 4 which illustrates Applicants' biocompatible glaucoma drainage device 200 having been implanted into the structure of eye 100 of FIG. 1. The catheter 330 provides a conduit for flow of aqueous humor from aperture 302 to porous assembly 210, wherein that aqueous humor is released by porous assembly 210 into surrounding tissue via the first and second porous elements 310 and 320. Using Applicants' method, end 510 of catheter 330 is surgically implanted into the anterior chamber 22 of eye 100. After surgical implantation into the sclera, the plurality of raised barbs 232 extending outwardly from anchoring assembly 230 engage with the surrounding tissue to prevent movement out of the eye. Furthermore, the "hub" 240 prevents movement of the implanted device further into the eye.

Thus, when Applicants' biocompatible glaucoma drainage device 200 (FIG. 2) is implanted into the eye 20 (FIG. 1), aqueous humor may flow from the anterior chamber 22 into aperture 302 of the catheter 330 and then flow into bore 675 formed in porous portion 210. Because first porous element 310 and second porous element 320 comprise a plurality of pores 720 and 660, respectively, extending therethrough, the aqueous humor may flow out of bore 675 and be absorbed by surrounding tissue. Further, because the first porous element 310 is formed to include a plurality of pores 720 sufficient in diameter to allow blood vessels to pass through or onto the surface, a stimulation of new blood vessels in this area can be achieved. In addition, because the second porous element 320 is formed to include a plurality of pores 660 which prevent cellular entry, the new stimulated blood vessels are prevented from entering bore 675, thereby maintaining the integrity of bore 675.

In certain embodiments, the biocompatibility of Applicants' glaucoma drainage device is enhanced (i.e., modified) with specific chemical agents (for example and without limitation natural protein tissue growth promoting factors) so that the subsequent healing response of tissue in association with the material forming the regions is altered once the glaucoma drainage device is implanted. The alteration in healing response is defined as a reduction in inflammatory response typically seen with polymeric materials, and includes a reduced presence of macrophages and foreign body giant cells.

In certain embodiments, the chemical modifications include the covalent interaction of the chemical species with polymer, by using, for example, a process provided by SurModics Inc. under the trademark PHOTOLINK. In certain embodiments, the chemical modifications include the absorption of the applied chemical species into the polymers. These chemical modifications include the use of proteins and peptides with known affects on cellular function, such as the reduction in inflammation, reduction in fibrous capsule formation by inhibiting the proliferation of cells found in developing fibrous capsules, inhibition of extracellular matrix protein synthesis by cells in the fibrous capsule, and/or stimulation of angiogenesis from existing vessels in the tissue surrounding the catheter and base plate of the implanted glaucoma drainage device. In certain embodiments, the chemical treatment includes any one, or a combination of, extracellular matrix proteins selected from the group consisting of collagen type I, collagen type III, collagen type IV, osteopontin, laminin type 1, laminin type 5, laminin type 10/11, fibronenctin, and peptide sequence RGD.

Further, a "denucleated" material reduces the inflammatory response of tissue surrounding the implant, and increases neovascularization (i.e., increase in new blood vessels) in tissue surrounding the material. In certain embodiments, Applicants' glaucoma drainage device 200 comprises a material(s) selected from the group consisting of denucleated polytetrafluoroethylene (ePTFE), denucleated polyurethane, and denucleated elastomeric silicone, such that at least 60% of air trapped within the material is removed. Denucleation is a process which removes air trapped within the material. Denucleation is defined as any process that effectively removes entrapped air from the porous regions of the device prior to or after surgical placement.

A preferred process for denucleating the device utilizes anhydrous ethanol, in which the device is soaked for a period of time (as short as 1-2 minutes) which may include storage, followed by slow dilution with alcohol containing increasing concentrations of sterile water, and finally pure, sterile water. In this way, entrapped air is effectively removed that would otherwise interfere with fluid wetting and transport after surgical placement in the eye of the patient.

The modification of surface properties of implantable polymers and the process of denucleation is described in more detail in the document "Denucleation promotes neovascularization of ePTFE in vivo," by Boswell et al, J. Biomater. Sci. Polymer Edn, Vol 0, No. 0, pp. 1-11 (1998), which is herein incorporated by reference in its entirety. Further, the process of denucleation is also described by Klitzman et al, J. Biomed. Mater. Res. 29, 1039 (1995), which is herein incorporated by reference in its entirety.

The following example is presented to further illustrate to persons skilled in the art how to make and use the invention. This example is not intended as a limitation, however, upon the scope of the invention.

EXAMPLE

This example describes the implantation of a denucleated ePTFE shunt of the present invention and its performance, including the healing and functional characteristics of the novel drainage device of this invention.

A 10 year-old neutered male Boston terrier had developed angle closure glaucoma secondary to uveitis with collapse of the ciliary cleft following earlier phacoemulsification with placement of an intraocular lens (IOL). Despite maximal glaucoma medications including topical carbonic anhydrase inhibitors and prostaglandin F2 alpha analogs (latanoprost) the intraocular pressure could not be controlled and implantation of the denucleated ePTFE device was elected in an attempt to preserve the eye. Routine preoperative preparation of the eye was conducted as for intraocular surgery. The device was placed in a subconjunctival tunnel with the tube passed into the anterior chamber via a tunneled incision in the superotemporal limbal sclera. The conjunctiva was closed with a running suture of 7-0 polyglactin 910. Fibrin occlusion of the tube in the anterior chamber occurred in the initial postoperative week and was treated by 2 injections of tissue plasminogen activator into the anterior chamber. Postoperative treatments consisted of the routine administration of oral antibiotics and non-steroidal anti-inflammatory agents as well as topical antibiotics and corticosteroids. Initially the intraocular pressure was low, but intraocular pressure increases have required the application of topical carbonic anhydrase inhibitors and latanoprost. After 3 months the intraocular pressure has remained controlled at <20 mmHg with the presence of the ePTFE device and 3 topical glaucoma medications [latanoprost 0.005%, dorzolamide 2% with timolol 0.5% (generic Cosopt), and compounded demecarium bromide 0.125%]. The device remains covered by the conjunctiva and intraocular pressure is controlled when prior to implantation it could not be controlled with medications alone.

Assessments and postoperative examinations are ongoing, and the eye is stable.

NIH guidelines for the care and use of laboratory animals (NIH Publication #85-23 Rev. 1985) were observed throughout this example.

The denucleated ePTFE device was designed to accept aqueous fluid between the surface of the eye and the polymer, rather than onto the surface of the device, and thus no bleb was formed. A space was seen under the ePTFE disk, presumably where fluid collected, but the overall thickness of the device with associated tissues was less than half of that observed with the commercial Baerveldt device (data not shown).

These results indicate that the denucleated ePTFE can act as a functional aqueous drainage device material, providing a maintenance of IOP at levels comparable with competitive shunts.

In addition, the close proximity of vessels to the denucleated ePTFE drainage device, as compared with the Baerveldt shunt, illustrates the novel material and design improve the functionality of the device. The vessel caliber around the denucleated ePTFE region of the device is suggestive of a microcirculation network, that portion of the circulation which can reabsorb interstitial fluids. Aqueous humor is a fluid with low colloid osmotic pressure, favoring diffusion into a site of higher colloid content such as blood. Thus, the presence of these vessels provides an additional source for reabsorption; in essence a surrogate to the episcleral vascular network.

Referring once again to FIG. 2, Applicants' method of making their glaucoma drainage device 200 includes sliding first porous element 310 over second porous element 320, and then thermally bonding that assembly to catheter 330 element using a bonding sleeve 240. The mechanical self-anchoring element 320 is provided by sliding another small section of this tubular material over the catheter 330, cutting the barb elements 232 by removing portions that tubular material, and then thermally bonding assembly 230 to catheter 330.

The surgical implantation of Applicants' biocompatible glaucoma drainage device 200 into a subject with glaucoma starts by denucleating device 200 in a non-aqueous solvent (ethanol is preferred) so as to remove at least 60% of air trapped within the first porous element 310 and the second porous element 320.

In certain embodiments, the denucleating step is performed using a graded series of alcohol baths followed by a series of washes with denucleated water to remove residual alcohol left by the alcohol baths. In certain embodiments, the denucleating step is performed using hyperbaric conditions defined as a high pressure greater than 250 mmHg while the device is submerged in an aqueous solution. In certain embodiments, the denucleating step is performed in a vacuum defined as a pressure less than 50 torr. In certain embodiments, device 200 is treated with extracellular matrix proteins selected from the group consisting of collagen type I, collagen type III, collagen type IV, osteopontin, laminin type 1, laminin type 5, laminin type 10/11, fibronenctin, and peptide sequence RGD. In certain embodiments, device 200 is stored in a denucleated aqueous environment until it is ready for use.

Further, a method of treating glaucoma using the above-noted novel glaucoma drainage device is provided. This method includes surgically inserting first end 510 catheter 330 into the anterior chamber of the eye, and anchoring or otherwise immobilizing the porous portion 210 end by (for example) using a tissue adhesive or dissolvable suture.

Applicants' glaucoma drainage device 200 has numerous advantages over the conventionally available glaucoma shunts. Some advantages are, for example, an improved healing response from surrounding tissues (e.g., improved biocompatibility), dramatic reduction in the formation of a dense, fibrous capsule around the device, and an increased life expectancy of the device. Further, in one example, the catheter is bonded to the outflow region and thus an extra bonding step may be omitted.

Numerous modifications and variations of the present invention are possible in light of the above teachings. It is therefore to be understood that within the scope of the appended claims, the invention may be practiced otherwise than as specifically described herein.

In the foregoing specification, the concepts have been described with reference to specific embodiments. However, one of ordinary skill in the art appreciates that various modifications and changes may be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

While the preferred embodiments of the present invention have been illustrated in detail, it should be apparent that modifications and adaptations to those embodiments may occur to one skilled in the art without departing from the scope of the present invention as set forth herein.

We claim:

1. A biocompatible glaucoma drainage device, comprising:
    a non-porous element having a first open end and a second open end;
    a porous element having an open end and an opposing closed end;
    wherein said second open end of said non-porous element is attached to said open end of said porous element;
    an anchoring assembly disposed around said non-porous element, wherein said anchoring assembly comprises a plurality of barbs extending outwardly therefrom;
    said non-porous element is formed to comprise a non-porous tubular member having a first lumen extending therethrough;
    said first lumen is formed to have a first diameter;
    said non-porous element further comprises a non-porous conical portion attached to said non-porous tubular member and flaring outwardly therefrom;
    said non-porous conical portion is formed to comprise a second lumen extending therethrough;
    said second lumen is formed to comprise said first diameter where said non-porous conical portion is attached to said non-porous tubular member;
    said second lumen is formed to comprise a second diameter at said second end of said non-porous element;
    said second diameter is greater than said first diameter;
    said porous element is formed to comprise a porous tubular member having a third lumen therein;
    said third lumen is formed to have a third diameter;
    said porous element further comprises a porous conical portion attached to said porous tubular member and flaring outwardly therefrom;
    said porous conical portion is formed to comprise said second diameter where said porous conical portion is attached to said non-porous conical portion;
    said second diameter is greater than said third diameter.

2. The biocompatible glaucoma drainage device of claim 1, wherein:
    said porous element comprises a first porous tubular member formed to include a first plurality of pores extending therethrough;
    each of said first plurality of pores is formed to comprise a diameter between about 30 microns to about 60 microns.

3. The biocompatible glaucoma drainage device of claim 2, wherein:
    said porous element comprises a second porous tubular member having an open end and an opposing closed end;
    said second porous tubular member is disposed around said first porous tubular member.

4. The biocompatible glaucoma drainage device of claim 3, wherein:
    said second porous tubular member is formed to include a second plurality of pores extending therethrough;
    each of said second plurality of pores is formed to comprise a diameter up to about 500 microns.

5. The biocompatible glaucoma drainage device of claim 1, wherein said porous element comprises a first plurality of pores; and each of said first plurality of pores is formed to comprise a diameter of about 0.8 microns.

6. The biocompatible glaucoma drainage device of claim 1, wherein said porous element comprises a permeability defined as a water flow through rate of at least 1.0 microliter/min·cm$^2$ at a water entry pressure of 100 mm Hg.

7. The biocompatible glaucoma drainage device of claim 1, wherein said non-porous element and said porous element are formed from materials selected from the group consisting of denucleated polytetrafluoroethylene (ePTFE), denucleated polyurethane, and denucleated elastomeric silicone, such that at least 60% of air trapped within the material is removed.

* * * * *